United States Patent
Taylor et al.

(10) Patent No.: US 6,300,367 B1
(45) Date of Patent: Oct. 9, 2001

(54) COMPOSITION FOR AND METHOD OF PREVENTING OR TREATING BREAST CANCER

(75) Inventors: Richard B. Taylor, Valley Park; E. C. Henley, St. Louis, both of MO (US)

(73) Assignee: Protein Technologies International, Inc., St. Louis, MO (US)

( * ) Notice: Subject to any disclaimer, the term of this patent is extended or adjusted under 35 U.S.C. 154(b) by 0 days.

(21) Appl. No.: 09/294,519

(22) Filed: Apr. 20, 1999

(51) Int. Cl.$^7$ .................... A61K 31/35; A61K 31/135

(52) U.S. Cl. ............................ 514/452; 514/648

(58) Field of Search .................... 514/648, 456

(56) References Cited

U.S. PATENT DOCUMENTS

| | | | |
|---|---|---|---|
| 4,133,814 | 1/1979 | Jones | 548/525 |
| 4,418,068 | 11/1983 | Jones | 514/337 |
| 4,696,949 | 9/1987 | Toivola et al. | 514/648 |
| 5,047,431 | 9/1991 | Schickaneder et al. | 514/648 |

FOREIGN PATENT DOCUMENTS 1-258669   10/1989   (JP).

OTHER PUBLICATIONS

Kawamura et al., Jpn. J. Pharmacol. 63(1), 27–34 Abstract Only, 1993.*
Wang et al., Nutr. Cancer, 31(2), 90–100 Abstract Only, 1993.*
A new triphenylethylene compound, Fc–1157a; Kallio et al., *Cancer Chemother. Pharmacol.*, 17:103–108; (1986).
A new triphenylethylene compound, Fc–1157a; Kangas et al., *Cancer Chemother. Pharmacol.*, 17:109–113; (1986).
Antiestrogenic Potency of Toremifene and Tamoxifen in Postmenopausal Women; Homesley et al., *Am J. Clin. Onc. (CCT)*; 16(2):117–122; (1993).
Pharmacologic and Biologic Properties of Droloxifene, A New Antiestrogen; Eppenberger et al.; *Am. J. Clin. Oncol. (CCT)*; 14(Suppl.2):S5–S14; (1991).
Droloxifene, a New Antiestrogen, in Advanced Breat Cancer; Deschênes; *Am. J. Clin. Oncol. (CCT)*; 14(Suppl.2):S52–S55; (1991).
Droloxifene, A New Antiestrogen; Kvinnsland; *Am. J. Clin. Oncol. (CCT)*; 14(Suppl.2):S46–S51; (1991).
Droloxifene, a New Estrogen Antagonist/Agonist, Prevents Bone Loss in Ovariectimized Rats; KE et al.; *Endrocrinology*; 136–:2435–2441; (1995).
Antagonism of Estrogen Action With a New Benzothiophene Derived Antiestrogen; Black et al.; *Life Sciences*; 32:1031–1036; (1983).
Raloxifene, A Selective Estrogen Receptor Modulator; Sato et al., *J. Bone Miner. Met.*; 12(Suppl.2):S9–S20; (1994).

Stereoselective Olefin Formation from the Dehydration of 1-(p–Alkoxphenyl)–1,2–diphenylbutan–1–ols: Application to the Synthesis of Tamoxifen; McCague, R.; *J. Chem. Soc. Perk. Trans.*; 1:1011–1015; (1987).
Derivatives of Tamoxifen, Dependence of Antiestrogenicity on the 4–Substituent; McCague et al.; *J. Med. Chem.*; 32(12):2527–2533; (1989).
Idoxifene: Report of a Phase I Study in Patients with Metastatic Breast Cancer; Coombes et al.; *Cancer Research*; 55:1070–1074: (Mar. 1, 1995).
Pyrrolidino–4–iodotamoxifen and 4–iodotamoxifen, New Analogues of he Antiestrogen Tamoxifen for the Treatment of Breast Cancer; Chander et al., *Cancer Research*; 51:5851–5858; (Nov. 1, 1991).
Non–Steroidal Antioestrogens—Receptor Binding and Biological Response In Rat Uterus, Rat Mammary Carcinoma and Human Breast Cancer Cells; Wakeling et al.; *J. Steroid Biochem.*; 20(1):111–120; (1984).
Genetic status of p53 and induction of apoptosis by radiation or isoflavones in human gastric carcinoma cell lines; Yanagihara et al.; *International Journal of Oncology*; 9:95–102; (1996).
Antiestrogens. 2. Structure–Activity Studies in a Series of 3–Aroyl–2arylbenzo[b]thiophene Derivatives Leading to [6–Hydroxy–2–(4–hydroxphenyl)benzo[b]thien–3–yl][4–[2–(1–piperdinyl)ethoxy]–phenyl]methanone Hydrochloride (LY 156758), a Remarkably Effective Estrogen Antagonist with Only Minimal Intrinsic Estrogenicity; Jones et al.; *J. Med. Chem.*; 27:1057–1066; (1984).
Effects of a New Antiestrogen, Keoxifene (LY156758), On Growth of Carcinogen–induced Mammary Tumors and on LH and Prolactin Levels; Clemens et al.; *Life Sciences*; 32(25):2869–2875; (1983).
Antagonism of Estrogen Action with a New Benzothiophene Derived Antiestrogen; Black et al.; *Life Sciences*; 32(9):1031–1036; (1983).

(List continued on next page.)

*Primary Examiner*—Jerome D. Goldberg
(74) *Attorney, Agent, or Firm*—Richard B. Taylor

(57) ABSTRACT

The present invention is a composition for preventing, minimizing, or reversing the development or growth of breast cancer. The composition contains a combination of a selective estrogen receptor modulator selected from at least one of raloxifene, droloxifene, toremifene, 4'-iodotamoxifen, and idoxifene and at least one isoflavone selected from genistein, daidzein, biochanin A, formononetin, and their respective naturally occurring glucosides and glucoside conjugates. The present invention also provides a method of preventing, minimizng, or reversing the development or growth of breast cancer in which a selective estrogen receptor modulator selected from at least one of raloxifene, droloxifene, toremifene, 4'-iodotamoxifen, and idoxifene is co-administered with at least one isoflavone selected from genistein, daidzein, biochanin A, formononetin, and their naturally occuring glucosides and glucoside conjugates to a woman having or predisposed to having breast cancer.

8 Claims, 4 Drawing Sheets

OTHER PUBLICATIONS

Chemoprevention of N–Nitrase–N–methylurea–induced Rat Mammary Cancer by Miso and Tamoxifen, Alone, and In Combination; Gotoh et al., *Jpn. J. Cancer Res.*; 89:487–495; (May 1998).

Selective Estrogen Receptor Modulation; Kauffman & Bryant; *DN&P;* 8(9):531–539; (Nov. 1995).

Dietary Estrogens Act Through Estrogen Receptor–Mediated Processes aand Show No Antiestrogenicity in Clutured Breast Cancer Cells; Mäkelä et al.; *Environmental Health Perspectives;* 102(6–7):572–578; (Jun.–Jul. 1994).

A Novel Mechanism for the Induction of Aromatase in Ovarian Cells in Vitro: Role of Transforming Growth Factor Alpha–induced Protein Tyrosine Kinase; Gangrade et al.; *Endocrinology*; 129(5):2790–2792; (1991).

Analysis of Estrogen Receptor Function in Vitro Reveals Three Distinct Classes of Antiestrogens; McDonnell et al.; *Molec. Endocrinology;* 9(6):659–669; (1995).

Genistein Arrests Cell Cycle Progression at $G_2$–M; Matsukawa et al., *Cancer Research*; 53:1328–1331; (Mar. 15, 1993).

Use of Tamoxifen for Breast Cancer; Twenty–Eight Years Later; Jaiyesimi et al.; *J. Clin. Oncology*; 13(2):513–529; (Feb. 1995).

Diet and Cancer: Markers, Prevention, and Treatment, Chap. 10—Potential Role of Dietary Isoflavones in the Prevention of Cancer; Barnes et al.; *Ed. M.M. Jacobs, Plenum Press,* NY, NY; pp. 135–147; (1994).

Physiological Effects of Phyto–oestrogens in Relation to Cancer and Other Human Health Risks; Cassidy; *Proceedings of the Nutrition Society*; 55:399–417: (1996).

Effects of Soya Consumption for One Month on Steroid Hormones in Premenopausal Women: Implications for Breast Cancer Risk Reduction; Lu et al.; *Cancer Epidemiology, Biomarkers; and Prevention;* 5:63–70; (Jan. 1996).

Antiproliferative Effects of Isoflavones on Human Cancer Cell Lines Established from the Gastrointestinal Tract; Yanagihara et al.; *Cancer Research*; 53:5815–5821; (Dec. 1, 1993).

Binding of Phyto–Oestrogen and Oestradiol–17β By Cytoplasmic Receptors in the Pituitary Gland and Hypothalamus of the Ewe; *J. Endocr.,* 85:317–325; (1980).

Genistein Inhibition of the Growth of Human Breast Cancer Cells: Independence From Estrogen Receptors and the Multi–Drug Resistance Gene; Peterson & Barnes; *Biochem. & Biophys. Res. Comm.*; 179(1):661–667; (1991).

Steroid and Phyto–oestrogen Binding to Sheep Uterine Receptors in Vitro; Shutt and Cox; *J. Endocrin.;* 52:299–310; (1972).

The Interaction in the Immature Mouse of Potent Oestrogens with Coumesterol, Genistein, and Other Utero–Vaginotrophic Compounds of Low Potency; Folman & Pope, *J. Endocrin.,* 34:215–225; (1966).

Effect of Soybean Isoflavones on Tumor Promoter–Induced $H_2O_2$ Production in Human Neutrophils and HL–60 Cells; Wei & Barnes; *Proceedings of the American Assn. For Cancer Research*; 34:167 (Mar. 1993); (Abstract).

Induction of Mammalian Topoisomerase II Dependent DNA Cleavage by Nonintercalcative Flavanoids, Genistein, and Orobol; Yamashita et al.; *Biochem. Pharmacol.;* 39(4):737–744; (1990).

Genistein, A Specific Inhibitor of Tyrosine–specific Protein Kinases; Akiyama et al.; *J. Biolog. Chem.;* 262(12):5592–5595; (Apr. 25, 1986).

The Role of Soy Products in Reducing Risk of Cancer; Messina and Barnes; *J. Nat. Canc. Inst.*; 83(8):541–546; (Apr. 17, 1991).

Mechanisms of Action in NIH–3t3 Cells of Genistein, an Inhibitor of EGF Receptor Tyrosine Kinase Activity; Linassier et al.; *Biochem. Pharmacol.*; 39(1):187–193; (1990).

Soybeans Inhibit Mammary Tumors in Models of Breast Cancer; Barnes et al.; *Mutagens and Carcinogens in the Diet*, Wiley–Liss pp. 239–253; (1990).

Effects of Hormonal Therapies and Dietary Soy Phytoestrogens on Vaginal Cytology in Surgically Postmenopausal Macques; Cline et al.; *Fertility and Sterility*; 65(5):1031–1035; (1996).

Non–steroidal Estrogens of Dietary Origin: Possible Roles in Hormone–Dependent Disease; Setchell et al.; *Am. J. Clin. Nutr.*; 40:569–578; (Sep. 1984).

In Vitro Hormonal Effects of Soybean Isoflavones; Molteni et al.; *J. Nutr.*; 125(3)Supp.:751–S–756S; (1995).

Soybean Phytoestrogen Intake and Cancer Risk; Adlercreutz et al.; *J. Nutr.*; 125(3)Supp.:757S–770S; (1995).

* cited by examiner

| Compound | R₁ | R₂ | R₃ | R₄ |
|---|---|---|---|---|
| Droloxifene | CH₃ | H | OH | NMe₂ |
| Toremifene | CH₂Cl | H | H | NMe₂ |
| 4'-Iodotamoxifen | CH₃ | I | H | NMe₂ |
| Idoxifene | CH₃ | I | H | pyrrolidino |

| Compound | R₁ | R₂ | R₃ | R₄ |
|---|---|---|---|---|
| Genistein | OH | H | OH | OH |
| Daidzein | OH | H | H | OH |
| Glycitein | OH | OCH₃ | H | OH |
| Biochanin A | OH | H | OH | OCH₃ |
| Formononetin | OH | H | H | OCH₃ |

| Compound | $R_1$ | $R_2$ | $R_3$ | $R_4$ |
|---|---|---|---|---|
| Genistin | H | H | OH | OH |
| 6'-OMal genistin | $COCH_2CO_2H$ | H | OH | OH |
| 6'-OAc genistin | $COCH_3$ | H | OH | OH |
| Daidzin | H | H | H | OH |
| 6'-OMal daidzin | $COCH_2CO_2H$ | H | H | OH |
| 6'-OAc daidzin | $COCH_3$ | H | H | OH |
| Glycitin | H | $OCH_3$ | H | OH |
| 6'-OMal glycitin | $COCH_3$ | $OCH_3$ | H | OH |

COMPOSITION FOR AND METHOD OF PREVENTING OR TREATING BREAST CANCER

FIELD OF THE INVENTION

The present invention relates to a composition containing a selective estrogen receptor modulator and at least one isoflavone, and a method of treating breast cancer while inhibiting selective estrogen receptor modulator induced uterotrophic effects.

BACKGROUND OF THE INVENTION

Breast cancer is one of the leading causes of cancer mortality among Western women, and is predicted to become a leading cause of cancer death in Oriental women in countries such as Japan in the near future. The American Cancer Society estimates that 1 in 9 women face a lifetime risk of this disease, which will prove fatal for about one-quarter of those afflicted with the disease.

Tamoxifen (FIG. 1), a synthetic nonsteroidal selective estrogen receptor modulator, has been used effectively in the treatment of breast cancer for over twenty years. Tamoxifen is one of the most widely prescribed antineoplastic agents in the United States and Great Britain, and is one of the initial hormonal treatments of choice in both premenopausal and postmenopausal women with estrogen receptor positive metastatic disease. Furthermore, adjuvant therapy studies show a substantial reduction of contralateral primary breast carcinoma in tamoxifen treated women, which indicates that tamoxifen may be of use in breast cancer prevention.

Tamoxifen has tissue-specific estrogenic and antiestrogenic effects. Estrogen, an ovarian hormone, increases the risk of breast and endometrial cancer by inducing an estrogen receptor mediated increase in the frequency of breast and endometrial cell division. Cell division is essential in the complex process of genesis of human cancer since it per se increases the risk of genetic error-particularly genetic errors such as inactivation of tumor suppressor genes.

Tamoxifen has antiestrogenic effects in breast tissue. Tamoxifen's antiestrogenic effect in breast tissue is a primary mechanism by which tamoxifen inhibits the proliferation of breast cancer cells. Tamoxifen competes with estrogen for binding to cytoplasmic estrogen receptors ("ER"), with subsequent inhibition by the tamoxifen/ER complex of many of the activities of endogenous estrogen within tumor cells. Endogenous estrogen binds with ERs to promote cellular activities such as estrogen/ER-mediated gene transcription, DNA synthesis, cancer cell growth, and increases in autocrine polypeptides such as transforming growth factor-alpha, epidermal growth factor, insulin-like growth factor-II, and other growth factors that may be involved in cell proliferation. Competitive inhibition of estrogen binding to ERs by tamoxifen reduces or prevents such cancer growth inducing cellular activities. As a result of tamoxifen's antiestrogenic activity in breast tissue, tamoxifen prevents the transition of breast cancer cells from the early G1 phase to the mid-G1 phase of the cell cycle and exhibits a cytostatic effect on breast cancer cells. Tamoxifen has been shown to reduce distant breast cancer metastasis as well as local-regional recurrence of such cancers in both node-negative and node-positive women.

Tamoxifen, however, has an estrogenic effect on uterine tissues when endogenous estrogen levels are low, which occurs in postmenopausal women and oopherectimized women. Uterine epithelial cell heights are significantly increased by the estrogenic effect of tamoxifen in postmenopausal and oopherectimized women, leading to uterine hypertrophy. Tamoxifen also causes marked uterine eosinophilia. These effects have been associated with endometrial carcinoma, and long term use of tamoxifen is linked to an increased risk of endometrial cancer, up to a fivefold excess of risk relative to women not treated with tamoxifen therapy. Therefore, application of tamoxifen for long term breast cancer prevention and long term treatment of breast cancer has significant associated risks.

Efforts have been made to develop new selective estrogen receptor modulators ("SERMS") which act in a mechanism similar to that of tamoxifen in breast tissue, while avoiding the risks caused by the estrogenic effects of tamoxifen in uterine tissue. Several of these SERMS are triphenylethylene tamoxifen analogs. As shown in FIG. 2, droloxifene is a tamoxifen analog in which a 3'-hydroxyphenyl moiety is substituted in place of a phenyl moiety of tamoxifen. Droloxifene has a binding affinity for the estrogen receptor which is ten times that of tamoxifen, has been shown to have antiestrogenic activity in breast tissue and to be efficacious in treatment of advanced breast cancer, yet has lower estrogenic effects in uterus tissue than tamoxifen. Droloxifene, a New Estrogen Antagonist/Agonist, Prevents Bone Loss in Ovariectomized Rats, Ke at al., *Endocrinology* 136:2435–2441 (1995).

Toremifene, shown in FIG. 2, is a tamoxifen analog having a 4-chloro substituent. Pharmacologically toremifene has quite similar effects as tamoxifen on breast tissue, acting as potent antiestrogen. Toremifene also exhibits anti-tumor cytolytic effects at high doses which are independent of its antiestogenicity, effects which do not occur with high doses of tamoxifen. Antiestrogenic Potency of Toremifene and Tarnoxifen in Postmenopausal Women, Homesley et al.,*Am. J. Clin. Onc.*, 16(2):117–122 (1993).

4-Iodotamoxifen, shown in FIG. 2, is another tamoxifen analog, having a 4'-iodophenyl substituent in place of a phenyl substituent of tamoxifen. Iodination of tamoxifen at the 4'-phenyl postion reduces estrogenic activity, mimicking the high antiestrogenic activity of the tamoxifen metabolite 4'-hydroxytamoxifen, while giving the compound a longer duration of action in vivo by blocking formation of the rapidly metabolized 4'-hydroxytamoxifen metabolite. Pyrrolidino-4-iodotamoxifen and 4-Iodotamoxifen, New Analogues of the Antiestrogen Tamoxifen for the Treatment of Breast Cancer, Chander et al., *Cancer Research*, 51:5851–5858 (Nov. 1, 1991); Idoxifene: Report of a Phase I Study in Patients with Metastatic Breast Cancer, Coombes et al, *Cancer Research*, 55:1070–1074 (Mar. 1, 1995). 4-Iodotamoxifen has been shown to have less estrogenic agonist activity in uterine tissue than tamoxifen, and, therefore, is less likely to cause endometrial cancer when administered over a long term.

Idoxifene, also known as pyrrolidino-4-iodotamoxifen, shown in FIG. 2, is another tamoxifen analog, and is modeled on the 4'-iodotamoxifen analog. Idoxifene has the same general molecular structure as 4'-iodotamoxifen, except that the N,N-dimethylamino moiety of 4'-iodotamoxifen is replaced with a pyrrolidino moiety. Substitution of the pyrrolidino group for the dimethylamino group reduces possible toxic side effects by inhibiting the metabolization of the compound by the liver to a desmethyl metabolite with the concomitant release of potentially toxic formaldehyde. Idoxifene has a 2.5 to 5 fold higher affinity for ERs than tamoxifen, and is 1.5-fold more effective in inhibiting the growth of MCF-7 breast cancer cells. Idoxifene also has less uterotrophic estogenic effects than tamoxifen and 4'-iodotamoxifen, and produced uterotrophic effects comparable to that of tamoxifen only at a dose which was ten times greater. Pyrrrolidino4-Iodotamoxifen and 4-Iodotamoxifen, New Analogues of the Antiestrogen Tamoxifen for the Treatment of Breast Cancer, Chander et al., *Cancer Research*, 51:5851–5858 (November 1991); Idoxifene: Report of a Phase I Study in Patients with Metastatic Breast Cancer, Coombes et al., *Cancer Research*, 55:1070–1074 (Mar. 1, 1995).

Other SERMS which are not tamoxifen analogs have shown effectiveness in preventing or minimizing the development of breast cancer. Raloxifene (FIG. 3), a benzothiophene derivative, has shown potent antiestrogenic inhibition of estradiol binding to the ER and significantly inhibits estrogen dependent proliferation of MCF-7 cells derived from human mammary tissue. Raloxifene, unlike tamoxifen and its analogs, exhibits an antiestrogenic effect in uterine tissue, and provides a nearly complete blockade of uterotrophic responses to estrogen as well as tamoxifen. Selective Estrogen Receptor Modulators, Kauffman & Bryant, *DN&P*, 8(9) 531–539 (November 1995).

It is desirable to utilize these SERMS to develop new compositions which may be used to improve the SERMS' prevention or minimization of the development of breast cancer while reducing their uterotrophic activity, if any.

SUMMARY OF THE INVENTION

In one aspect, the present invention is a composition for preventing or minimizing the development or growth of breast cancer. The composition comprises a combination of a selective estrogen receptor modulator selected from at least one of raloxifene, droloxifene, toremifene, 4-iodotamoxifen, and idoxifene, and at least one isoflavone selected from genistein daidzein, biochanin A, formononetin, or their respective naturally occuring glucosides or glucoside conjugates.

In another aspect, the present invention is a method for preventing or minimizing the development or growth of breast cancer in a human. A selective estrogen receptor modulator and an isoflavone are co-administered to a human to prevent or minimize the development or growth of breast cancer. The selective estrogen receptor is selected from at least one of raloxifene, droloxifene, toremifene, 4'-iodotamoxifen, and idoxifene. The isoflavone is selected from at least one of genistein, daidzein, biochanin A, formononetin, or their naturally occuring glucosides or glucoside conjugates.

DESCRIPTION OF THE PREFERRED EMBODIMENTS

As used herein, the term "ER" refers to "estrogen receptor". The term "breast cancer" means any cancer having its origin in breast cells, and includes metastatic and local forms of breast cancer (node negative and node positive), as well as ER positive and ER negative forms of breast cancer. The term "uterotrophic effect" means the proliferation of uterine epithelial cells, which frequently is a side effect of administration of selective estrogen receptor modulators to women, and which appears to be directly related to development of endometrial cancer. As used herein "Mal" represents "malonyl" and "Ac" represents "acetyl". The term "minimize", or a derivative thereof, includes a complete or partial inhibition of a specified biological effect (which is apparent from the context in which the term minimize is used). The term "isoflavone" may mean both a single isoflavone or plural isoflavones when the isoflavone is defined as at least one of a selected group of isoflavones. "SERM" means a selective estrogen receptor modulator and its physiologically acceptable salts, other than tamoxifen, which is a compound which produces estrogen antagonist effects in one or more desired target tissues (e.g. breast tissue and uterine tissue), while producing either estrogen agonist effects or minimal agonism in other non-target tissues.

Figure 4:
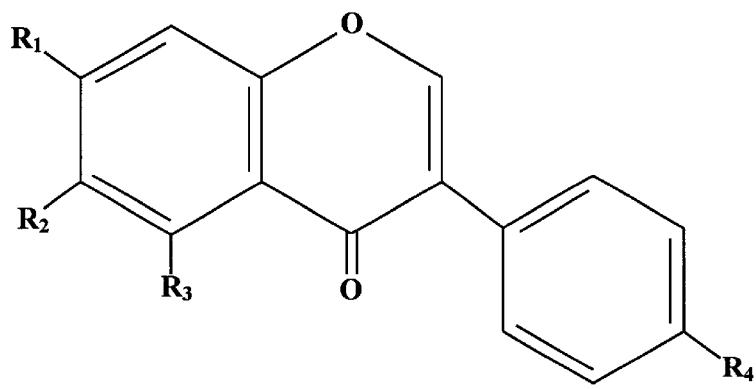
FIG. 4 is a molecular representation of genistein, daidzein, biochanin A, and formononetin.
Figure 5:
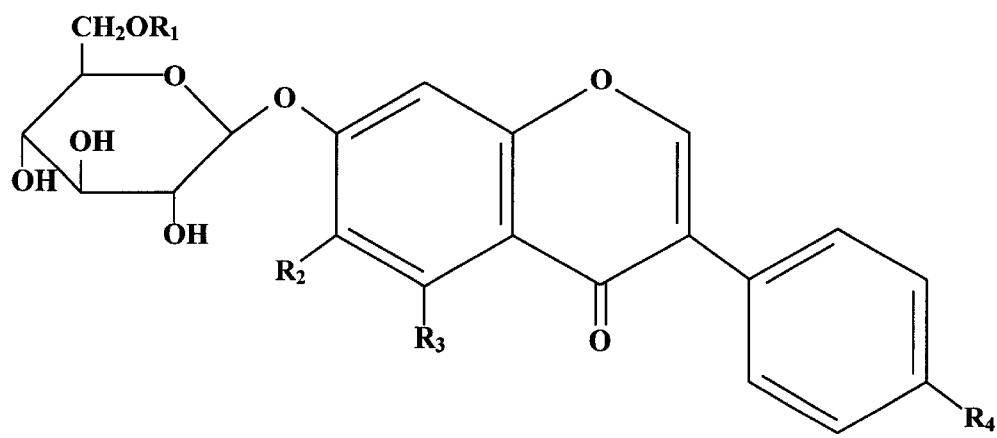
FIG. 5 is a molecular representation of the naturally occuring glucosides of genistein and daidzein.

The present invention resides in the discovery that the combination of selected SERMs with certain isoflavones can be used to treat or prevent breast cancer in a woman having or predisposed to breast cancer, and the isoflavones will augment the SERM induced prevention, minimization, or reversal of the development or growth of breast cancer, as well as prevent or minimize uterotrophic effects associated with some SERMs. The SERMs which are useful in the compositions and methods of the present invention are droloxifene, toremifene, 4'-iodotamoxifen, idoxifene, and raloxifene. The isoflavones which are useful in the compositions and methods of the present invention are genistein, daidzein, glycitein, biochanin A, formononetin, their naturally occuring glycosides and their naturally occuring glycoside conjugates, shown in FIGS. 4 and 5.

Materials

Figure 1:
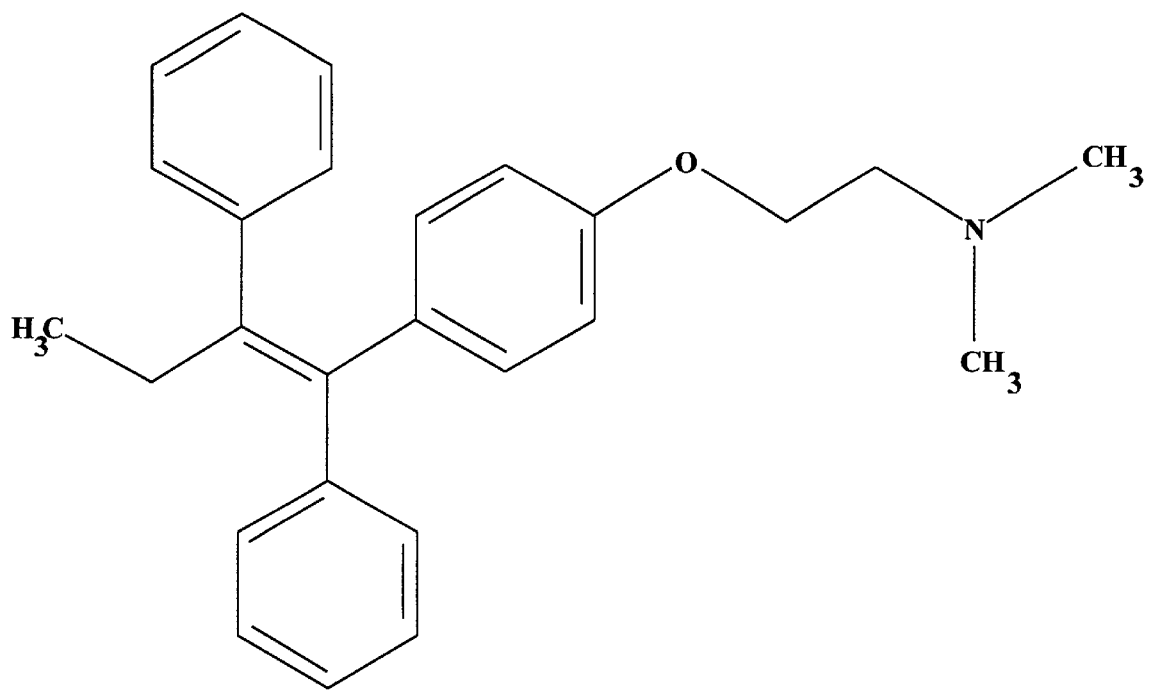
FIG. 1 is a molecular representation of tamoxifen.
Figure 2:
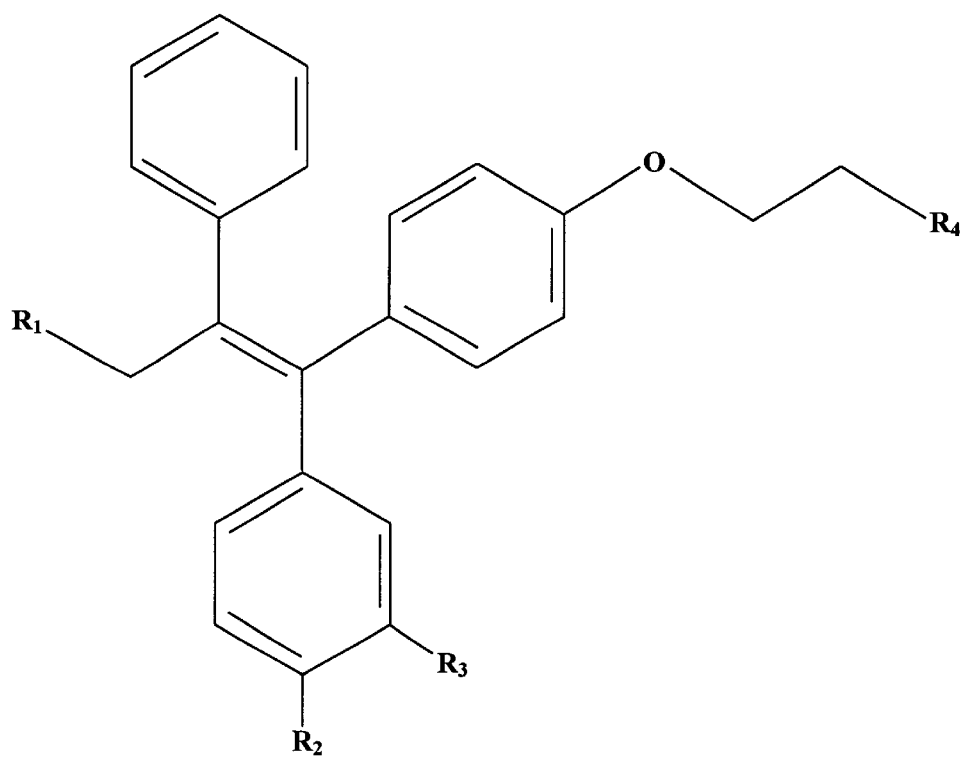
FIG. 2 is a molecular representation of the selective estrogen receptor modulators droloxifene, toremifene, 4'iodotamoxifen, and idoxifene.
Figure 3:
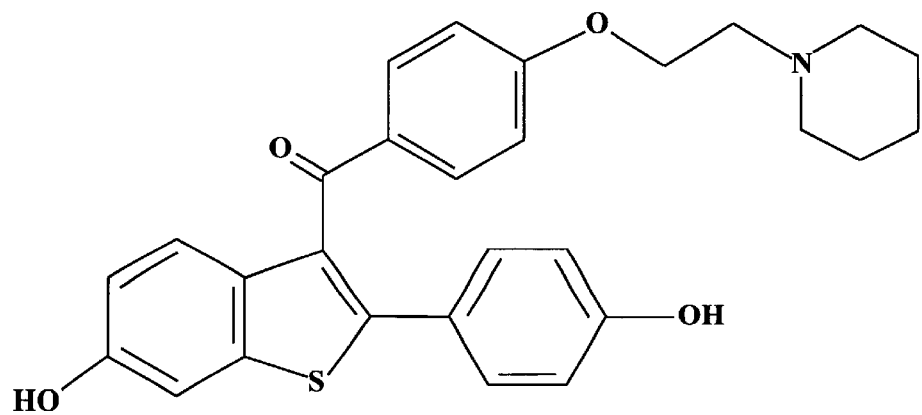
FIG. 3 is a molecular representation of the selective estrogen receptor modulator raloxifene.

The selective estrogen receptor modulator compounds used in the compositions and methods of the present invention can be chemically synthesized according to known methods, and include the salt forms of each of the compounds. Raloxifene, 6-hydroxy-2(4-hydroxyphenyl)-3-[4-(2-piperdinoethoxy)benzoyl]benzo[b]thiophene (FIG. 3), and its physiologically acceptable salts may be produced according to the methods described in U.S. Pat. Nos. 4,418,068 and 4,133,814, each of which is incorporated herein by reference. Droloxifene, E-1-[4'-(2-dimethylaminoethoxy) phenyl]-1-(3'-hydroxyphenyl)-2-phenyl-1-butene (FIG. 2), and its physiologically acceptable salts may be produced according to the methods described in U.S. Pat. No. 5,047,431, which is incorporated herein by reference. Toremifene, 4-chloro-1,2-diphenyl-1-{4-[2-(N,N-dimethylamino) ethoxy]-phenyl}-1-butene (FIG. 2), and its physiologically acceptable salts may be produced by the methods described in U.S. Pat. No. 4,696,949, which is incorporated herein by reference. 4'-Iodotamoxifen, E-1-{4-[2-(dimethylamino) ethoxy]phenyl}-1-(4-iodophenyl)-2-phenyl-1-butene (FIG. 2), and its physiologically acceptable salts may be produced according to combined methods described in Stereoselective Olefin Formation from the Dehydration of 1-(p-Alkoxyphenyl)-1,2-diphenylbutan-1-ols: Application to the Synthesis of Tamoxifen, McCague, *J. Chem. Soc. Perkin Trans.*, 1:1011–1015 (1987); and Derivatives of Tamoxifen. Dependence of Antiestrogenicity on the 4-Substituent, McCague et al., *J. Med. Chem.*, 32(12):2527–2533 (1989), each of which is incorporated herein by reference. Idoxifene, E-1-(4-iodophenyl)-1-[14(2-pyrrolidinoethoxy)phenyl]-2-phenyl-1-butene (FIG. 2), may be produced according to combined methods described in the references above that provide methods for producing 4'-iodotamoxifen.

The isoflavone compounds used in the compositions and methods of the present invention are naturally occurring substances which may be found in plants such as legumes, clover, and the root of the kudzu vine (pueraria root). Common legume sources of these isoflavone compounds include soy beans, chick peas, and various other types of beans and peas. Clover sources of these isoflavone compounds include red clover and subterranean clover. Soy beans are a particularly preferred source of the isoflavone compounds (except biochanin A which is not present in soy).

The isoflavone compounds may be isolated from the plant sources in which they naturally occur, or may be synthetically prepared by processes known in the art. For example, daidzein may be isolated from red clover as disclosed by Wong (*J. Sci. Food Agr.*, Vol. 13, p. 304 (1962)) or may be isolated from the mold *Micromonospora halophytica* as provided by Ganguly and Sarre (*Chem. & Ind. (London)*, p. 201 (1970)), both references of which are incorporated by reference herein. Daidzein may be synthetically prepared by the methods provided by Baker et al (*J Chem. Soc.*, p. 274 (1933)), Wesley et al. (*Ber.* Vol. 66, p. 685 (1933)), Mahal et al. (*J. Chem. Soc.*, p. 1769 (1934)), Baker et al. (*J. Chem. Soc.*, p. 1852 (1953)), or Farkas (*Ber.* Vol. 90, p. 2940 (1957)), each reference of which is incorporated herein by reference. The isoflavone glucoside daidzin may be synthetically prepared by the method of Farkas et al. (*Ber.*, Vol. 92, p. 819 (1959)), incorporated herein by reference. The daidzein isoflavone glucoside conjugates 6'-O-Mal daidzin and 6'-O-Ac daidzin can be prepared by a conventional saponification of daidzin with a malonyl or an acetyl anhydride, respectively.

Genistein may be synthetically prepared by the methods provided by Baker et al (*J. Chem. Soc.*, p. 3115 (1928)); Narasimhachari et al. (*J. Sci. Ind. Res.*, Vol. 12, p. 287 (1953)); Yoder et al., (*Proc. Iowa Acad. Sci.*, Vol. 61, p. 271 (1954); and Zemplen et al. (*Acta. Chim. Acad. Sci. Hung.*, Vol. 19, p. 277 (1959)), each reference of which is incorporated herein by reference. The isoflavone glucoside genistin may be synthetically prepared by the method of Zemplen et al. (*Ber.*, Vol 76B, p. 1110 (1943)), incorporated herein by reference. The isoflavone glucoside conjugates of genistein, 6'-O-Mal genistin and 6'-O-Ac genistin, can be prepared by a conventional saponification of genistin with a malonyl or an acetyl anhydride, respectively.

Biochanin A can be synthetically prepared by the method provided by Baker et al. (*Nature* 169:706 (1952)), incorporated herein by reference. Biochanin A can also be separated from red clover by the method provided by Pope et al. (*Chem. & Ind. (London)* p.1092 (1953)), incorporated herein by reference. Formononetin can be synthetically prepared by the methods disclosed by Wessely et al. (*Ber.* 66:685 (1933)) and Kagel et al. (*Tetrahedron Letters*, p. 593 (1962)), both references of which are incorporated herein by reference. Formononetin can be isolated from soybean meal by the method of Walz (*Ann.* 489:118 (1931)) or can be isolated from clover species by the method of Bradbury et al. (*J. Chem. Soc.* p. 3447 (1951)), both references of which are incorporated herein by reference.

It is preferred to extract the isoflavones useful in the compositions and methods of the present invention from the plant materials in which they naturally occur. A preferred method of isolating the isoflavone compounds is to extract the plant materials with an alcohol, preferably methanol or ethanol, or an aqueous solution, preferably an aqueous alkaline solution, to remove the isoflavones from the plant material. It is preferred to comminute the plant material before extracting the isoflavone compounds to maximize recovery of the isoflavone compounds from the plant material. The isoflavone compounds can be isolated from the extract by conventional separation procedures such as reverse phase high performance liquid chromatography ("HPLC").

In a preferred embodiment, the isoflavone compounds genistein, genistin, 6'-O-Mal genistin, 6'-O-Ac genistin, daidzein, daidzin, 6'-O-Mal daidzin, 6'-O-Ac daidzin, glycitein, glycitin, and 6'-O-Mal glycitin are isolated from a soy material, preferably a commercially available soy material. Soy materials from which the isoflavone compounds can be isolated include: soy beans, dehulled soy beans, soy meal, soy flour, soy grits, soy flakes (full fat and defatted), soy cotyldeons, soy molasses, soy protein concentrate, soy whey, soy whey protein, and soy protein isolate. In one embodiment, the isoflavones are extracted from soy beans, dehulled soy beans, soy meal, soy flour, soy grits, soy flakes, soy protein concentrate, soy whey protein, or soy protein isolate, preferably soy meal, soy flour, soy grits, or soy flakes, with a low molecular weight organic extractant, preferably an alcohol, ethyl acetate, acetone, or ether, and most preferably aqueous ethyl alcohol or methyl alcohol. Most preferably the extractant has a pH at about the isoelectric point of soy protein (about pH 4 to pH 5) to minimize the amount of soy protein extracted by the extractant.

The extractant containing the isoflavones is separated from the insoluble soy materials to form an isoflavone enriched extract. If desired, an isoflavone enriched material may be recovered by concentrating the extract to remove the solvent, thereby producing a solid isoflavone enriched material.

In a more preferred embodiment the isoflavone compounds are further purified from other soy materials soluble in the extract by contacting the extract with a material which adsorbs the isoflavones in the extract, and eluting the adsorbed isoflavones out of the adsorbent material with a solvent which causes the isoflavones to be differentially eluted from the adsorbent material.

In a preferred embodiment, the isoflavones are separated from impurities in the extract by a conventional reverse phase HPLC separation. After extraction of the isoflavones from the soy material and separation of the extract from the insoluble soy materials, the extract is filtered to remove insoluble materials that could plug an HPLC column. An HPLC column is prepared by packing a conventional commercially available HPLC column with a particulate adsorbent material which will releasably bind the isoflavones and impurities in the extract in a compound specific manner. The adsorbent material may be any reverse phase HPLC packing material, however, a preferred packing material may be chosen by the criteria of load capacity, separation effectiveness, and cost. One such preferred packing material is Kromasil C18 16 $\mu$m 100 Å beads available from Eka Nobel, Nobel Industries, Sweden.

The filtered extract is passed through the packed HPLC column until all the binding sites of the column are fully saturated with isoflavones, which is detected by the appearance of isoflavones in the effluent from the column. The HPLC column may then be eluted with a solvent to effect the separation. In a preferred embodiment, the eluent is a polar solvent such as ethanol, methanol, ethyl acetate, or acetonitrile, and preferably is an aqueous alcohol having an alcohol content of between about 30% and about 90%, most preferably about 50%, and most preferably the alcohol is ethanol.

The isoflavone compounds and impurities are separately collected from the column effluent. The isoflavone fractions of the eluent may be identified from other eluent fractions in accordance with conventional HPLC and analytical chemistry techniques. In a preferred embodiment the eluent fractions containing the aglucone isoflavones are collected separately since the aglucone isoflavones are believed to be particularly active tyrosine kinase inhibitors and anti-angiogenesis agents which inhibit the development or progression of breast cancer. Of the aglucone isoflavone materials, the fraction of effluent containing daidzein elutes from the column first, followed by a glycitein fraction, followed by the more polar genistein.

The isoflavone fractions of the eluent may be collected from the column, and the volatile content of the solvent (e.g. alcohol) can be removed by evaporation. The isoflavone compounds can be recovered directly if all of the solvent is removed by evaporation, or may be recovered by chilling the remaining solvent (e.g. water) to crystallize the isoflavones and centrifuging or filtering the remaining solvent away from the crystallized isoflavones.

In a particularly preferred embodiment the soy isoflavone glucosides and isoflavone glucoside conjugates—6'-O-Mal genistin, 6'-O-Ac genistin, 6'-O-Mal daidzin, 6'-O-Ac daidzin, 6'-O-Mal glycitin, genistin, daidzin, and glycitin—are converted to their respective aglucone isoflavone forms—genistein, daidzein, and glycitein. The conversion of the isoflavone glucoside conjugates and the isoflavone glucosides to the aglucone isoflavones can be effected in the substrate from which the isoflavones are to be extracted prior to the extraction, or may be effected in the isoflavone enriched extract after separation of the extract from the insoluble materials. The aglucone isoflavone compounds are especially desirable in the compositions and methods of the present invention since, as noted above, they are believed to be particularly active in inhibiting angiogenesis and inhibiting tyrosine kinase activity.

The isoflavone glucoside conjugates 6"-O-Mal genistin, 6"-O-Ac genistin, 6"-O-Mal daidzin, 6"-O-Ac daidzin, and 6"-O-Mal glycitin can be converted to their respective glucosides genistin, daidzin, and glycitin by forming an aqueous alkaline solution of the substrate containing the isoflavones having a pH of about 6 to about 13, preferably about pH 9 to about pH 11, and treating the aqueous alkaline solution at a temperature of about 2° C. to about 121° C., preferably about 25° C. to about 75° C., for a period of time sufficient to effect the conversion, preferably about 30 minutes to about 5 hours, more preferably about 30 minutes to about 1.5 hours. The isoflavone glucosides genistin, daidzin, and glycitin can be converted to their respective aglucone forms genistein, daidzein, and glycitein by contacting the isoflavone glucosides with an enzyme capable of cleaving a 1,4-β-glucoside bond—preferably a commercially available beta-glucosidase enzyme, an alpha- or beta-galactosidase enzyme, a pectinase enzyme, a lactase enzyme, or a gluco-amylase enzyme—at a pH at which the enzyme is active, typically from about pH 3 to about pH 9, and at a temperature of about 25° C. to about 75° C., more preferably about 45° C. to about 65° C., for a period of time sufficient to effect the conversion, typically about 1 hour to about 24 hours, preferably about 1 hour to about 3 hours.

The aglucone isoflavones can be separated from the substrate using conventional separation procedures. For example, the aglucone isoflavones may be extracted from the substrate with a low molecular weight alcohol. The aglucone isoflavones may be separated from the extract by conventional recrystallization processes, or by HPLC. In a particularly preferred embodiment, an isoflavone composition isolated from a soy substrate for formulation into a composition for use in the method of the present invention includes at least 40% genistein, at least 15% daidzein, and at least 1% glycitein. In another particularly preferred embodiment of the invention, an isoflavone composition isolated from a soy substrate for formulation into a composition for use in the method of the present invention contains at least 85% genistein, at least 5% daidzein, and at least 0.5% glycitein. In yet another preferred embodiment, each isoflavone is recovered separately in pure form.

Several of the isoflavone compounds are commercially available, and may be purchased for formulation into compositions provided in the present invention, or used in the methods of the present invention. For example, genistein, daidzein, and glycitein are commercially available and may be purchased, for example, from Indofine Chemical Company Inc., P.O. Box 473, Somerville, N.J. No. 08876, and biochanin A is available from Aldrich Chemical Company, Inc., 940 West Saint Paul Avenue, Milwaukee, Wis. 53233.

Methods

In one aspect the present invention is a method for preventing or minimizing the development or growth of breast cancer in a human by co-administering at least one SERM selected from raloxifene, droloxifene, toremifene, 4-iodotamoxifen, and idoxifene, and at least one isoflavone selected from genistein, daidzein, biochanin A, formononetin, their respective glucosides, and their respective glucoside conjugates. The SERM and isoflavone may be co-administered prophylactically to prevent the development of breast cancer in women susceptible of developing breast cancer, or the SERM and isoflavone may be co-administered to treat breast cancer by preventing, minimizing, or reversing the growth and development of the cancer. The SERM may be obtained for use in accordance with the method the present invention as described above, or, preferably, may be provided in a composition of the present invention, as described below. The isoflavone may be obtained for use in accordance with the method of the present invention as described above, or, preferably, may be provided in a composition of the present invention, as described below.

The SERM and the isoflavone may be co-administered either concurrently or sequentially within a specified period of time, preferably daily, on a periodic basis. Most preferably the SERM and the isoflavone are co-administered concurrently in a composition of the present invention, as described below, on a periodic basis, preferably daily. Alternatively, the SERM and the isoflavone are administered sequentially as separate components. "Sequentially" as used herein is intended to mean administration of desired amounts of the SERM and isoflavone individually within a specified periodic period of time, for example daily, and is not intended to be limited to immediate consecutive administration of the SERM and isoflavone.

The SERM is administered in an amount sufficient to prevent or treat the development or growth of breast cancer in combination with the isoflavone. The amount of SERM sufficient to prevent or treat the development or growth of breast cancer in combination with the isoflavone is dependent on the particular SERM utilized, the amount and activity of the isoflavone utilized, the size of the patient to which the SERM is administered, whether the SERM is administered prophylatically or to treat breast cancer, and if used in treatment, the extent of the cancer. The amount of SERM sufficient to prevent the development of breast cancer in a woman predisposed to breast cancer is preferably at least 0.5 mg per day, more preferably from about 0.5 mg to about 100 mg per day, and most preferably from about 5 mg to about 50 mg per day. The amount of SERM sufficient to treat the development or growth of breast cancer to prevent, minimize, or reverse the development or growth of the cancer is preferably at least 0.5 mg per day, more preferably from 0.5 mg to about 500 mg per day, and most preferably from about 40 mg to about 400 mg per day. The SERM may be administered in several doses per day to achieve the daily amount of the SERM sufficient to prevent or treat breast cancer, however, it is preferred that the daily required amount of SERM be administered in one or two doses.

The isoflavone is co-administered to the human in an amount sufficient to prevent or treat the development or growth of breast cancer in combination with the SERM. The amount of isoflavone sufficient to prevent or treat the development or growth of breast cancer in combination with the SERM is dependent on the particular isoflavone utilized, the amount and activity of the co-administered SERM, the size of the patient, whether the isoflavone is administered prophylatically or to treat breast cancer, and if used in treatment, the extent of the cancer. The amount of isoflavone sufficient to prevent the development of breast cancer in a woman predisposed to breast cancer in the present method is preferably at least 1 mg per day, more preferably from about 10 mg to about 200 mg per day. The amount of isoflavone sufficient to treat the development or growth of breast cancer to prevent, minimize, or reverse the development or growth of the cancer is preferably at least 1 mg per day, more preferably from about 1 mg to about 1000 mg per day, and most preferably from about 50 mg to about 500 mg per day.

The isoflavones utilized in the method of the present invention prevent, minimize, or reverse the growth of breast cancer by several mechanisms, which in combination with the anti-estrogenic activity of the SERM in breast tissue, increase the relative anti-breast cancer activity of each compound. First, the isoflavones are anti-estrogenic in breast tissue, and serve to competitively inhibit estrogen induced cancerous breast cell division by binding to the ER of the cell, where the isoflavone/ER complex inhibits cancer cell growth in much the same manner as tamoxifen and the SERMs (e.g. daidzein halts cell growth in the G1 phase of the cell cycle, and genistein halts cell growth in the G2 phase of the cell cycle). Second, some of the isoflavones, particularly genistein and biochanin A, and to a lesser extent daidzein and formononetin, are tyrosine kinase inhibitors which inhibit enzymatic tyrosine kinase activity. Tyrosine kinase activity is necessary for cancerous cells to produce proteins required for cellular differentiation and growth. Third, the isoflavones inhibit angiogenesis, thereby preventing a cancerous cell mass from developing the network of blood vessels necessary to support the cell mass, limiting the sustainable growth of the cell mass. Fourth, the isoflavones decrease endogenous estrogen levels by interfering with pituitary and hypothalmus gland feedback mechanisms which regulate the release of gonadotropins such as estradiol. The effect of the combined mechanisms of action is to further prevent or minimize the development or growth of breast cancer when co-administered with a SERM effective to prevent or minimize the growth of breast cancer.

In a particularly preferred embodiment of the method of the present invention, the isoflavone is co-administered with the SERM in an amount sufficient to prevent or minimize SERM induced uterotrophic effects. Atlhough the SERMs utilized in the present invention are less uterotrophic than tamoxifen, each of the SERMs except raloxifene induces uterotrophic effects at relatively high doses. The isoflavones utilized in the present method have an antiestrogenic effect in uterine tissues when concenrations of estrogen or an estrogen agonist SERM are relatively high. One mechanism by which the isoflavones likely cause an antiestrogenic effect in uterine tissue in the presence of uterine estrogen agonist SERMs is by binding to uterine cell ERs and competitively inhibiting the estrogen agonist SERMs from binding to the ERs. Unlike uterine tissue estrogen agonist SERMs, the isoflavones do not cause an estrogenic response upon binding to uterine cell ERs, therefore, the isoflavones prevent, inhibit, or minimize the uterotrophic effects caused by uterine endothelial cell ER/SERM complexes. Preferably the isoflavone is co-administered with the SERM to prevent or minimize uterotrophic effects in a weight/weight ratio of isoflavone:SERM of about 0.25:1 to about 100:1, and more preferably from about 0.5:1 to about 20:1.

In a particularly preferred embodiment of the method, co-administration of the isoflavone with a uterine tissue estrogen agonist SERM in an amount sufficient to prevent or minimize uterotrophic effects is also effective to prevent or minimize the development of endometrial cancer when the SERM is used to prevent or treat breast cancer. As noted above, tamoxifen and uterine tissue estrogen agonist SERMs cause an increased risk of the development of endometrial cancer as a result of estrogen-like activity in uterine tissue and its uterotrophic effects. Co-administration of the isoflavone together with an uterine tissue estrogen agonist SERM prevents or minimizes the development of endometrial cancer by preventing or minimizing SERM induced uterotrophic effects.

Compositions

In another aspect, the present invention is a composition useful for preventing or minimizing the development or growth of breast cancer. The composition includes combination of a selective estrogen receptor modulator selected from at least one of raloxifene, droloxifene, toremifene, 4-iodotamoxifen, and idoxifene, and at least one isoflavone selected from genistein, daidzein, biochanin A, formononetin, their respective naturally occuring glucosides and glucoside conjugates. These SERM and isoflavone materials necessary to form compositions in accordance with the present invention may be obtained as described above. The composition contains from about 1% to about 99% SERM, by weight of biologically active ingredients, and from about 1% to about 99% isoflavone, by weight of biologically active ingredients.

The SERM is present in the composition in an amount sufficient to prevent, minimize, or reverse the development or growth of breast cancer in a woman when co-administered with the isoflavone. Preferably at least 0.5 mg of the SERM is present in the composition, more preferably from about 0.5 mg to about 500 mg, and most preferably from about 5 mg to about 100 mg. Most preferably, the SERM is present in the composition in an amount sufficient to prevent, minimize, or reverse the development or growth of breast cancer by itself.

Preferably at least 1 mg of the isoflavone is present in the composition, more preferably from about 1 mg to about 1000 mg, and most preferably from about 10 mg to about 200 mg. In a preferred embodiment the isoflavone is present in the composition in an amount sufficient to augment the composition's SERM induced prevention or minimization of development or growth of breast cancer when the composition is administered to a woman. In a more preferred embodiment, the isoflavone is present in the composition in an amount sufficient to prevent, minimize, or reverse the development or growth of breast cancer by itself.

In another preferred embodiment, the isoflavone is present in the composition in an amount sufficient to prevent or minimize the composition's SERM induced uterotrophic effects when the composition is administered to a woman. The isoflavone should be present in a ratio of isoflavone:SERM of from about 0.25:1 to about 100:1 by weight, and more preferably from about 0.5:1 to about 50:1 by weight, to be present in the composition in an amount sufficient to prevent or minimize the composition's SERM induced uterotrophic effects. In a most preferred embodiment, the isoflavone is present in the composition in an amount sufficient to augment the composition's SERM induced prevention or minimization of the development or growth of breast cancer and to prevent or minimize the composition's SERM induced uterotrophic effects when the composition is administered to a woman.

A composition in accordance with the present invention containing a SERM and an isoflavone can be prepared by conventional procedures for blending and mixing compounds. Preferably, the composition also includes an excipient, most preferably a pharmacuetical excipient. Compositions containing an excipient and incorporating the SERM and isoflavone can be prepared by procedures known in the art. For example, the SERM and the isoflavone can be formulated into tablets, capsules, powders, suspensions, solutions for parenteral administration including intravenous, intramuscular, and subcutaneous administration, and into solutions for application onto patches for transdermal application with common and conventional carriers, binders, diluents, and excipients.

Inert pharmaceutically acceptable carriers useful to form pharmaceutical compositions in accordance with the present invention include starch, mannitol, calcium sulfate, dicalcium phosphate, magnesium stearate, silicic derivatives, and/or sugars such as sucrose, lactose, and glucose. Binding agents include carboxymethyl cellulose and other cellulose derivatives, gelatin, natural and synthetic gums including alginates such as sodium alginate, polyethylene glycol, waxes and the like. Diluents useful in the invention include a suitable oil, saline, sugar solutions such as aqueous dextrose or aqueous glucose, and glycols such as polyethylene or polypropylene glycol. Other excipients include lubricants such as sodium oleate, sodium acetate, sodium stearate, sodium chloride, sodium benzoate, talc, and magnesium stearate, and the like; disintegrating agents including agar, calcium carbonate, sodium bicarbonate, starch, xanthan gum, and the like; and adsorptive carriers such as bentonite and kaolin. Coloring and flavoring agents may also be added to the pharmaceutical compositions.

The following nonlimiting formulations illustrate pharmaceutical compositions of the present invention.

FORMULATIONS

The following Formulations 1–4 illustrate pharmaceutical formulations including a SERM and an isoflavone.

Formulation 1

Gelatin capsules

Hard gelatin capsules are prepared using the following ingredients: SERM 0.5–100 mg/capsule; Isoflavone 0.1–1000 mg/capsule; Starch, NF 0–600 mg/capsule; Starch flowable powder 0–600 mg/capsule; Silicone fluid 350 centistokes 0–20 mg/capsule. The ingredients are mixed, passed through a sieve, and filled into capsules.

Formulation 2

Tablets

Tablets are prepared using the following ingredients: SERM 0.5–100 mg/tablet; Isoflavone 0.1–1000 mg/tablet; Microcrystalline cellulose 20–300 mg/tablet; Starch 0–50 mg/tablet; Magnesium stearate or stearate acid 0–15 mg/tablet; Silicon dioxide, fumed 0–400 mg/tablet; silicon dioxide, colloidal 0–1 mg/tablet, and lactose 0–100 mg/tablet. The ingredients are blended and compressed to form tablets.

Formulation 3

Suspensions

Suspensions are prepared using the following ingredients: SERM 0.5–100 mg/5 ml; Isoflavone 0.1–1000 mg/5 ml; Sodium carboxymethyl cellulose 50–700 mg/5 ml; Sodium benzoate 0–10 mg/5 ml; Purified water 5 ml; and flavor and color agents as needed.

Formulation 4

Parenteral Solutions

A parenteral composition is prepared by stirring 1.5% by weight of active ingredients (SERM and isoflavone wt/wt ratio of from 10:1 to 1:10) in 10% by volume propylene glycol and water. The solution is made isotonic with sodium chloride and sterilized.

The above description is intended to be illustrative of the present invention, and is not intended to be limiting. Other embodiments are within the claims.

What is claimed is:

1. A composition for preventing, minimizing, or reversing the development or growth of breast cancer in a woman comprising a combination of droloxifene and genistein, wherein said droloxifene is present in said composition in an amount effective to prevent, minimize, or reverse the development or growth of breast cancer in a woman upon adminstration to said woman, and said genistein is present in said composition in an amount effective to prevent or minimize uterotrophic effects induced by said droloxifene in said woman and without treating the cancer.

2. The composition of claim 1 wherein from about 0.5 mg to about 500 mg of droloxifene is present in said composition.

3. The composition of claim 2, wherein from about 5 mg to about 100 mg of droloxifene is present in said composition.

4. The composition of claim 1 wherein said genistein is present in an amount sufficient to augment prevention or minimization of development or growth of breast cancer provided by droloxifene upon administration of said composition to a woman.

5. The composition of claim 1 wherein from about 1 mg to about 1000 mg of genistein is present in said composition.

6. The composition of claim 5 wherein from about 10 mg to about 200 mg of genistein is present in said composition.

7. The composition of claim 1 further comprising an excipient.

8. The composition of claim 7 wherein droloxifene, genistein, and said excipient are combined into a pharmaceutical preparation.

* * * * *